United States Patent [19]

Purdie

[11] Patent Number: 5,246,864
[45] Date of Patent: Sep. 21, 1993

[54] CIRCULAR DICHROISM AND SPECTROPHOTOMETRIC ABSORPTION DETECTION METHODS

[75] Inventor: Neil Purdie, Stillwater, Okla.

[73] Assignee: Research Corporation Technologies, Inc., Tucson, Ariz.

[21] Appl. No.: 639,222

[22] Filed: Jan. 9, 1991

Related U.S. Application Data

[63] Continuation-in-part of Ser. No. 463,473, Jan. 11, 1990, abandoned.

[51] Int. Cl.$^5$ .................. G01N 33/92; G01N 21/31
[52] U.S. Cl. ................................ 436/71; 436/91; 436/92; 436/93; 435/11
[58] Field of Search .............. 436/71, 171, 63, 91–93; 435/11; 356/39, 222

[56] References Cited

U.S. PATENT DOCUMENTS

| | | | |
|---|---|---|---|
| 3,884,638 | 5/1975 | Dixon et al. | 436/71 |
| 4,486,531 | 12/1984 | Ziegenhorn | 435/19 |
| 5,118,613 | 6/1992 | McGowan | 435/11 |

OTHER PUBLICATIONS

Purdie et al. "Analytical Applications of Polarmetry, Optical Rotatory Dispersion and Circular Dichroism", Anal. Chem. vol. 61, No. 2 Jan. 15, 1989 pp 77A–89A.
Chemical Abstracts, vol. 108, No. 24, Abstract No. 210070, (Jun. 1988).
Chemical Abstracts, vol. 98, No. 20, Abstract NO. 166955 (May 1983).
Chemical Abstracts, vol. 84, No. 19, Abstract No. 132207 (May 1976).
Lambert et al., Org. Struct. Anal., Macmillan, NY (1976), pp. 325–332.
Grahnen et al., Clinica Chimica Acta, 52 (1974), pp. 187–197.
Kannel et al., Annals of Int. Medicine, vol. 74, No. 1, (1971) pp. 1–12.
Castelli et al., JAMA, vol. 256, No. 20, (1986), pp. 2835–2838.
Abbott et al., Arteriosclerosis, vol. 3, No. 3, (May/Jun. 1983) pp. 260–272.
Clinical Chemistry, vol. 34, (1988), pp. 193–201.
Superko et al., JAMA, vol. 256, No. 19 (Nov. 1986), pp. 2714–2717.
Warnick et al., Clincal Chemistry, vol. 26, No. 1, (1980) pp. 169–170.
Grundy et al., Arch. Intern. Med., vol. 149, (Mar. 1989), pp. 505–510.
Cox and Spencer, Canadian Journ. of Chemistry, vol. 29, pp. 217–222.
Baillie et al., 43rd Natl. Mtg. Am. Ass. for Clinical Chem., 1991, Workshop Report.
Warnick et al., 43rd Natl. Mtg. Am. Ass. for Clinical Chem., 1991, Roundtable Report.

*Primary Examiner*—James C. Housel
*Assistant Examiner*—David Redding
*Attorney, Agent, or Firm*—Birch, Stewart, Kolasch & Birch

[57] ABSTRACT

Spectrophotometric methods, including the use of convention spectroscopic absorption or circular dichroism, for clinical chemistry detection methods. More specifically, with the use of such spectrophotometric methods in the measurement of cholesterol levels and direct measurement of cholesterol subfractions in clinical samples, and in the measurement of lipoprotein levels in a clinical test sample, as well as in the detection of anabolic steroids and other steroid products. The invention is also concerned with providing certain CD and conventional spectrophotometric apparatus useful in each of the aforesaid chemical methods.

38 Claims, 7 Drawing Sheets

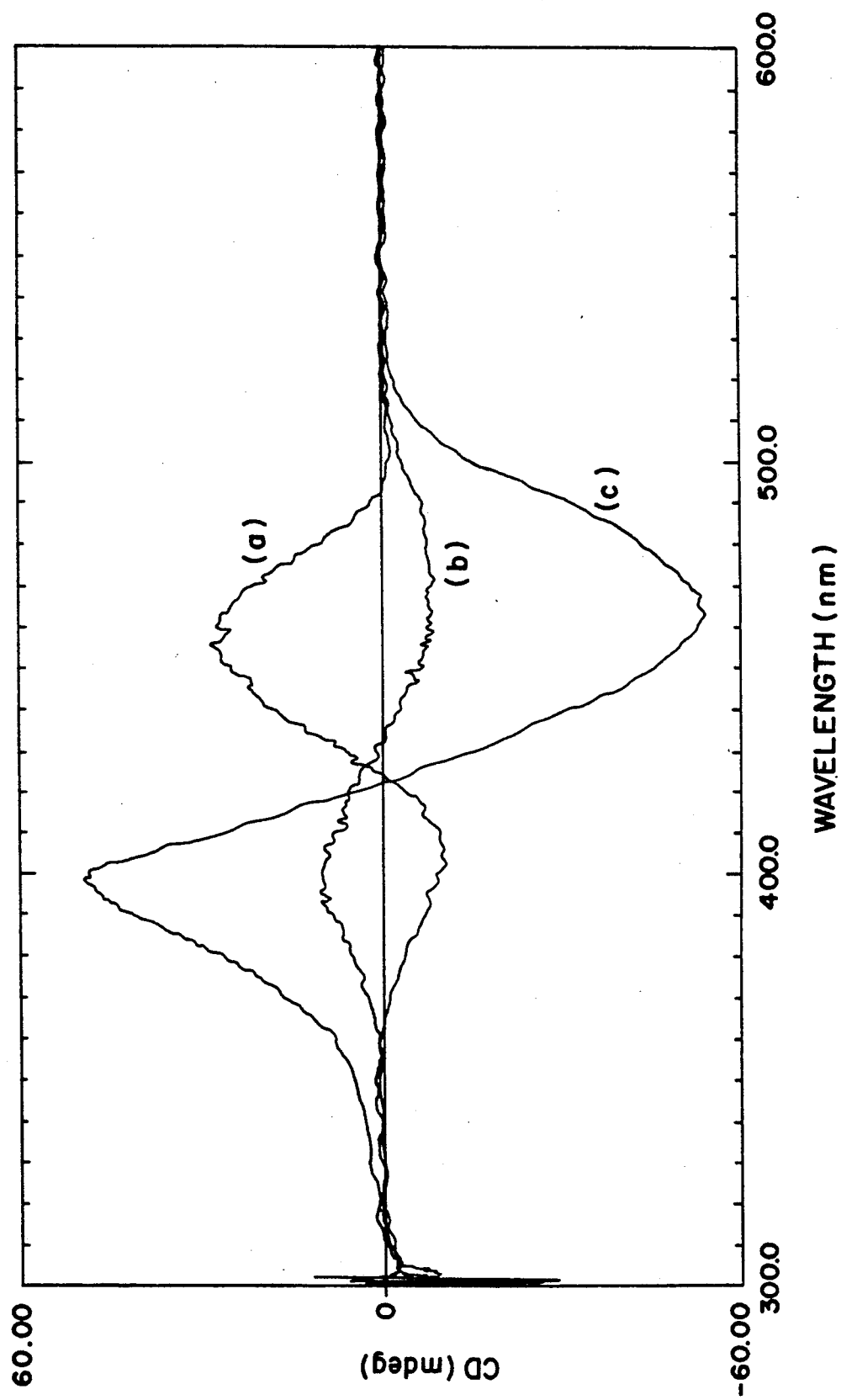

CIRCULAR DICHROISM AND SPECTROPHOTOMETRIC ABSORPTION DETECTION METHODS

The present application is a continuation-in-part application of copending application Ser. No. 07/463,473, filed on Jan. 11, 1990, now abandoned, which is expressly incorporated by reference herein.

FIELD OF THE INVENTION

The present invention is concerned with the use of circular dichroism and absorption detection in clinical chemistry detection methods. More specifically, with their use in the measurement of cholesterol levels an direct measurement of cholesterol subfractions in clinical samples, as well as in the detection of anabolic steroids and other steroid products, and in the measurement of lipoprotein levels in a serum test sample. The invention is also concerned with providing certain CD and absorption apparatuses useful in each of the aforesaid chemical methods.

BACKGROUND OF THE INVENTION

Spectrophotometric absorption refers to the measurement of the absorption or transmission of incident light through solutions of test compounds. Typically, compounds of interest have characteristic absorption spectra, transmitting or absorbing specific wavelengths of light, which can be used to determine the presence of these compounds in test samples. Instruments designed for spectrophotometric absorption have a light source, for which the emitted wavelength is known and may be adjusted, and one or more detectors sensitive to desired wavelengths of transmitted light. Spectrophotometric absorption can be used to determine the amounts of a given compound that are present in a test sample.

Circular dichroism is a special type of absorption method in which the molecular composition of the compound results in differential absorption of incident light not only at a specific wavelength but also of a particular polarization state. Circular dichroism is a chiroptical method which allows one to differentiate between different enantiomers, that is, optical isomers having one or more asymmetric carbon atom (chiral) centers. When utilizing CD, generally a sample is illuminated by two circularly polarized beams of light traveling in unison. Both beams pass through the sample simultaneously and are absorbed. If the sample is optically active, the beams are absorbed to a different extent. The differences in absorption of the beams can then be displayed as a function of the wavelength of the incident light beam as a CD spectrum. No difference in absorption is observed for optically inactive absorbers so that these compounds are not detected by a CD detecting system. The use of CD as a chiroptical method has been fully described in scientific literature (1).

Early applications of the CD method primarily dealt with elucidation of molecular structures, especially natural products for which a technique capable of confirming or establishing absolute stereochemistry was critical. However, CD has also reportedly been used in a clinical method to quantitatively determine unconjugated bilirubin in blood plasma (2). In the method disclosed, a complex was formed between bilirubin and human serum albumin as a CD probe for bilirubin analysis.

Clinical applications of circular dichroism are also discussed by Neil Purdie and Kathy A. Swallows in *Analytical Chemistry*, Vol. 61, No. 2, pp 77A–89A (1989), herein incorporated by reference. Possible clinical applications of CD are disclosed to include measurement of cholesterol levels and detection of anabolic steroids. However, suitable chemical reagents for carrying out such testing are not disclosed.

Regarding the use of spectrophotometric absorption or CD methods and apparatus herein disclosed to measure cholesterol levels, it is noted that the population at large is continually advised that it is prudent to know serum cholesterol levels and constantly reminded that an uncontrolled diet and a lack of exercise can lead to accumulation of arterial plaque that will increase the risk of atherosclerosis and coronary heart disease. Statistical studies have shown that other risk factors, such as age, gender, heredity, tobacco and alcohol consumption, etc. must also be considered when counselling patients about the risks (3,4).

The magnitude of the program for screening the general public is so immense that automated methods for cholesterol determinations are necessary. These tests currently used differ in complexity from the simple dip-stick approach, which uses a color sensitive reaction on a paper support, to the sophisticated lipid profile tests, in which the distribution of cholesterol among the various solubilizing molecular species is determined (5). The dip-stick is only a preliminary qualitative test upon which a decision for the fuller, more quantitative measurement can be based.

At the conclusion of a recent extensive study of how health risk factors are related to elevated levels of serum cholesterol, a report (6) was prepared by the Laboratory Standardization Panel (LSP) of the National Cholesterol Education Program (NCEP) in which the measure of risk was correlated with three ranges of total cholesterol (TC): low risk if less than 200 mg/dL; marginal risk in the range 200–239 mg/dL; and high risk if greater than 240 mg/dL. In order to place a particular individual into one or other of these categories, all that is required is a serum TC measurement. The other risk factors (3,4) are then added as a basis for further patient counselling. This relatively simple approach replaces an earlier recommendation (3,7), in which relative risk was established using a ratio of TC to high density lipoprotein cholesterol (HDL-C) equal to 5. A ratio lower than 5 implies a high level of HDL-C and a low relative risk. For this diagnosis, HDL-C is measured in a second independent test.

The same report (6) hastened to add, that there were serious inaccuracies in measurements made by numerous clinical laboratories in the determination of the amount of TC present in human serum reference standards.

Statistically, the results showed that in data from 1500 laboratories, 47% failed to measure the true value to within a coefficient of variance (CV) of ±5% and 18% of these failed at a CV of ±10%. As a consequence, the LSP recommended that an improvement in CV to within ±3% for TC should be achieved by 1992. Recent surveys indicate that certified laboratories are well on their way to meeting that challenge, using the current clinical methods and instrumentation (8). The LSP did not report the inaccuracies associated with the determination of the distribution of cholesterol among the various lipids and lipoproteins, but did indicate that an evaluation would be made in the future. The very poor proficiency and lack of reliability in the measurement of serum or plasma HDL-C, has been eloquently described in three recent publications (7,9,10), where interlaboratory CV's as high as 38% were reported (9). A 1987 evaluation by the College of American Pathologists of the measurement of the sample for HDL-C by over two thousand laboratories showed, that more than one third differed by more than 5% from the reference value. Interlaboratory CV's among groups using the same method did improve to 16.5%, but it is still too imprecise to be of any predictive clinical value. This is the reason the TC:HDL-C ratio is no longer used in risk assessment, although it offers potential advantages in defining the true clinical picture.

Regarding the presently used lipid profile studies, cholesterol is distributed in the serum mainly associated with high density lipoprotein (HDL-C) and low density lipoprotein (LDL-C) fractions and with triglycerides as the very low density lipoprotein cholesterol (VLDL-C) fraction. There is plenty of statistical evidence from a number of long term clinical tests to justify that a high proportion of HDL-C and a low proportion of LDL-C is associated with lower relative risk (3,4) or in simpler terms, high levels of beneficial, provided the level is not excessively low, less than 30 mg/dL (7). VLDL-C cholesterol has not been implicated in any risk determination, but high triglyceride itself can be a serious problem. In a typical lipid profile study, total and HDL-C cholesterols are measured directly. VLDL-C is taken to be a fixed fraction (e.g, 0.2) of the triglyceride, which is also measured directly in a separate assay. LDL-C is calculated from these figures and is not measured directly. The propagation of errors in each of the three independent measurements makes LDL-C the fraction known with least overall accuracy, although it may be the most significant aspect of cardio-vascular risk. Because of this, it is difficult to meaningfully monitor and justify that clinical progress has been made in LDL-C reduction therapy with time.

Regarding the use of a CD method to detect anabolic steroids and other steroid products, it has been disclosed that ketosteroids are amenable to direct CD detection (11). Several anabolic steroids have also been shown to exhibit CD spectra that appear to be distinguishing (11).

SUMMARY OF THE INVENTION

An object of the present invention is to provide spectrophotometric methods for direct measurement of cholesterol in clinical samples, as it exists in association with several particular lipoprotein sub-fractions. These spectrophotometric methods encompass both CD and conventional absorption spectrophotometry, either separately or in combination. The CD methods permit measurement of anabolic steroids or other steroid products as well.

Another object of the present invention is to provide a method of measuring cholesterol levels in a clinical test sample, wherein the combined LDL-C+VLDL-C level is determined directly, or where LDL-C and VLDL-C levels separately can be directly determined, using either CD or spectrophotometric absorption. It is a further object of the present invention to provide a method wherein LDL-C, VLDL-C, combined LDL-C+VLDL-C and HDL-C levels in a test sample can all be determined directly, and simultaneously, if desired It is still a further object of the invention to combine direct measurement of cholesterol subfractions by CD absorption with the direct measurement of TC by spectrophotometric absorption, while using identical reaction conditions. It is also an object of the present invention to provide novel apparatuses to carry out such detection methods.

Another object of the present invention is to provide methods and apparatuses for detecting the presence of lipoproteins which are associated with different cholesterol subfractions.

Accordingly, the present invention provides for a clinical method for determining the amount of cholesterol, lipoprotein, anabolic steroid or other steroidal product in a serum test sample, by forming a reaction product with the cholesterol, lipoprotein anabolic steroid or other steroidal product in the test sample, and then either perform step (a), (a') or (a''):

Step (a) determining the CD and/or absorption of the test sample over a range from about 150 to 700 nm (preferably from about 240 nm to 625 nm);

Step (a') determining the CD absorption of the test sample at one or more discrete wavelengths within a range from about 150 to 700 nm (preferably from about 240 nm to 625 nm);

Step (a'') determining the spectrophotometric absorption spectrum of the test sample at one or more discrete wavelengths within a range from about 400 nm to 700 nm (preferably about 450 to 625 nm).

The invention further provides for apparatuses for practicing the present inventive methods, which apparatuses are exemplified, but not limited, by the following.

A detection instrument for determining the amount of VLDL-C+LDL-C, HDL-C and total cholesterol (TC) present in a test sample, the instrument including means for determining the amount of HDL-C present in the sample by CD absorption at a first wavelength or a first and a second wavelength, means for determining the amount of VLDL-C+LDL-C in the sample by CD absorption at a third wavelength, and means for determining the amount of TC in the sample by spectrophotometric absorption at the third wavelength, or alternatively, means for determining the amount of TC in the sample by calculation or computation, based upon values obtained for VLDL-C+LDL-C and HDL-C in the sample.

A detection instrument for determining the amount of VLDL-C+LDL-C, HDL-C and total cholesterol (TC) present in a sample, the instrument including means for determining the amount of TC in the sample by spectrophotometric absorption at a first wavelength, means for determining the amount of VLDL-C+LDL-C in the sample by CD absorption at the first wavelength, and means for determining the amount of HDL-C in the sample by calculation or computation, based upon values obtained for VLDL-C+LDL-C and TC in the sample.

A spectrophotometric absorption instrument for determining the amount of total cholesterol (TC), combined VLDL-C+LDL-C, and HDL-C present in a test sample, the instrument comprising spectrophotometric absorption means for directly determining the amount of TC in the sample at a first wavelength, spectrophotometric absorption means for directly determining HDL-C at a second wavelength, means for determining combined LDL-C+VLDL-C by computation using the values obtained for TC and HDL-C, and optionally spectrophotometric absorption means for directly determining the amount of VLDL-C in the test sample.

The following Glossary of Terms is provided to remove any ambiguity, which may exist as to the use of certain terms and abbreviations used herein.

The term "CD instrument" as used herein, means a Circular Dichroism Instrument Such instruments are available commercially or may be constructed from parts, which may be commercially available Additionally, FIG. 6 is included herewith to provide a simple schematic of how a CD works As can be seen in FIG. 6, light from a light source (LS) is linearly polarized with linear polarizers (P) and then circularly polarized in opposite directions by circular polarizers (Q) and then shown through a specimen cell (S), whereupon absorbance is measured by a detector (D), the difference is measured and plotted as a function of wavelength to produce a CD spectrum, or alternatively, may be recorded at preselected wavelengths.

The term "LDL cholesterol" (abbreviated LDL-C) as used herein, means low density lipoprotein cholesterol. The term "HDL cholesterol" (abbreviated HDL-C) as used herein, means high density lipoprotein cholesterol The term "VLDL cholesterol" (abbreviated VLDL-C) as used herein, means very low density lipoprotein cholesterol and the term "total cholesterol" (abbreviated TC) as used herein, means the sum of the cholesterol subfractions in a test sample, i.e., TC=HDL-C+LDL-C+VLDL-C. The term "Cholesterol Subfraction" as used herein, refers to HDL-C, LDL-C and VLDL-C.

The term "anabolic steroid" as used herein, means steroids such as testosterone and its 17-epimer, dehydrotestosterone, 17-alkyltestosterones, nortestosterone, mestanolone, methandriol and the like The term "steroidal products" as used herein, means other steroids, such as 17 ketosteroids, adrenal corticoids and the like.

The term "lipoprotein" as used herein, means macromolecular complexes of lipids and proteins found in human plasma. Exemplary of such lipoproteins are low density lipoprotein, very low density lipoprotein, intermediate density lipoprotein, $LP_{(a)}$ lipoproteins, chylomicrons, apolipoproteins (A-1, A-11, B-48, B-100, C, D, E, etc), and the like.

The term "Chugaev reaction product" as used herein, means the reaction product of cholesterol, an anabolic steroid or steroidal product or lipoprotein with Chugaev reactants such as 20% w/v $ZnCl_2$ in glacial acetic acid and 98% acetyl chloride, or the like The "Chugaev Reaction" utilized herein to form the Chugaev reaction products of the present invention, is disclosed in the literature (12) and is suggested to involve dehydration and opening of the B-ring of the steroid to form an optically active colored reaction product.

The term "test sample", "clinical test sample" or "serum test sample" as used herein, refers to a whole blood test sample or a whole blood test sample having the cell bodies removed therefrom by centrifugal force or through the use of an appropriate filter mechanism, both of which means are well known to those skilled in the art.

The term "bilirubin conjugate" as used herein, means the conjugate found between bilirubin and a serum lipoprotein, apolipoprotein or protein at about a pH of 5.0–5.1. Preferably, the conjugate is formed with a lipoprotein or apolipoprotein, which is associated with a cholesterol subfraction.

The term "spectrophotometric absorption" as used herein refers to measurement of the absorption (or, conversely, transmission) of incident light by colored compounds at specific wavelengths irrespective of the state of polarization of the light.

The term "alkali metal sulfate" as used herein, means sodium sulfate, lithium sulfate, potassium sulfate, and the like, wherein a sulfate salt is formed with an alkali metal.

The term "alkali earth metal sulfate" as used herein, means calcium sulfate, barium sulfate, and the like, wherein a sulfate salt is formed with an alkali earth metal.

The term "transition metal sulfate" as used herein, means scandium sulfate, titanium sulfate, chromium sulfate, manganese sulfate, nickel sulfate, zinc sulfate, copper sulfate, cadmium sulfate, and the like, wherein a sulfate salt is formed with a transition metal.

The term "alkali metal perchlorate" as used herein, means sodium perchlorate, lithium perchlorate, potassium perchlorate, or the like, wherein a perchlorate salt is formed with an alkali metal.

BRIEF DESCRIPTION OF THE DRAWINGS

The present invention will more fully understood from the detailed description given here and below and the accompanying drawings which are given by way of illustration only, and thus, are not limitative of the present invention.

FIG. 5(a) is a graph that shows the pH dependence of the CD spectrum of the Human Serum Albumin+Bilirubin conjugate; Curve (a)=pH 5.6; Curve (b)=pH 4.8; and Curve (c)=pH 4.4.

FIG. 6 is a schematic of a CD, wherein:

LS is the high intensity conventional light source or laser source; M1 and M2 are monochromators required for full spectral data; P is the linearly polarizing element; Q is the circularly polarizing element; S is the sample cell; D is the detector (of which there may be up to three); and REC is the recorder.

Figure 7:
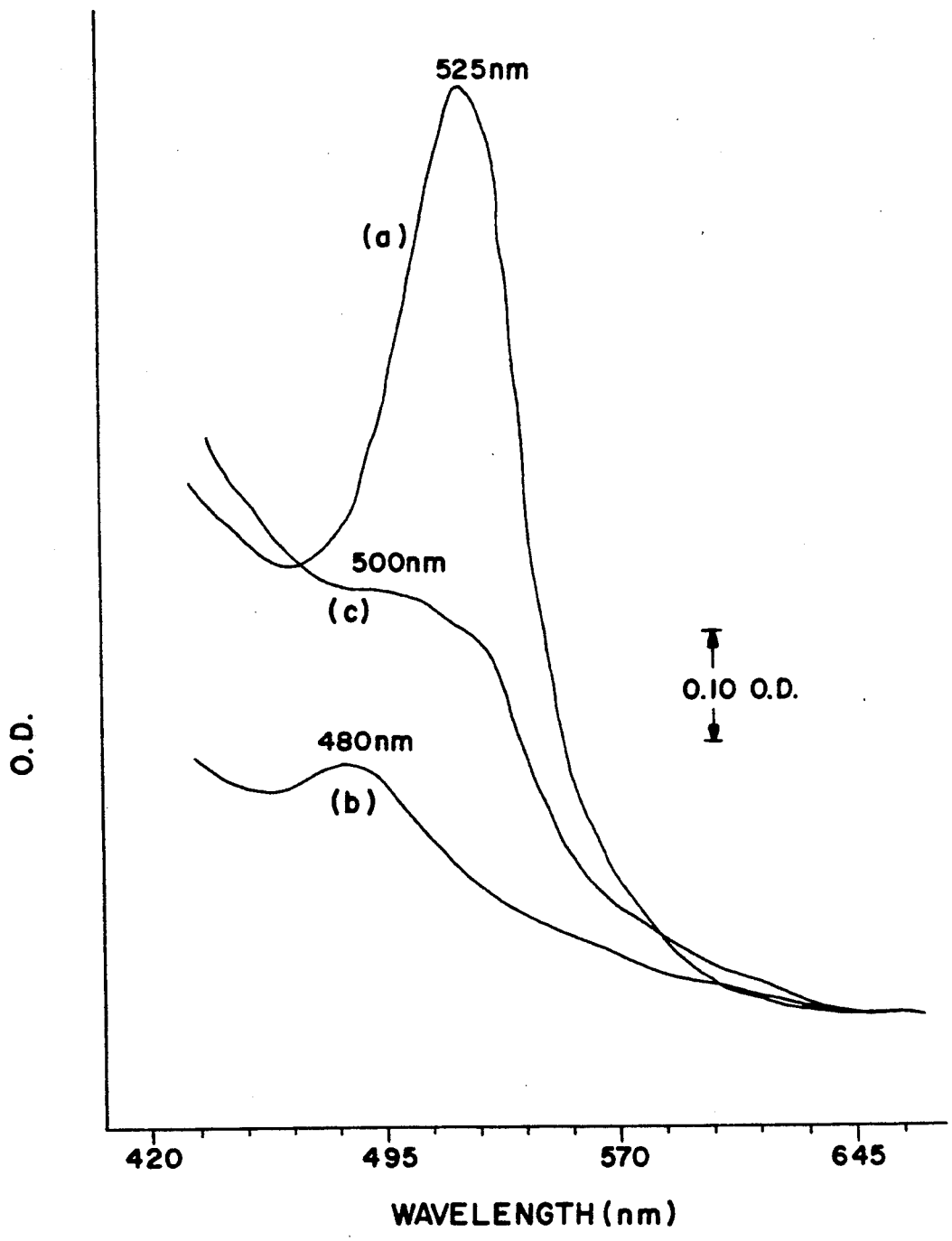

FIG. 7 is a graph that shows the normal absorption spectrum of the optically active colored product obtained from the reaction of Chugaev reagents with cholesterol, wherein:

Absorption Curve(a) is observed after reaction of the sample with the Chugaev reagent;

Absorption Curve (b) is observed after reaction with the Chugaev reagent to which has been added approximately 2% w/v $Na_2SO_4$ or other alkali metal or alkaline earth metal sulfate; and Absorption Curve (c) is observed after reaction with the Chugaev reagent to which has been added approximately 2% w/v dextran sulfate or alkali metal perchlorate such as sodium perchlorate.

DETAILED DESCRIPTION OF THE INVENTION

The following detailed description of the present invention is provided as an aid in the practice of the present invention. Much of the discussion appearing herein relates to methods and instruments for determining the amount of cholesterol and cholesterol subfractions present in a test sample, however, the present invention should not be considered to be unduly limited by such discussions. This is true, since those skilled in the art will generally understand that the present inventive methods and apparatus can be used to measure the presence of a wide variety of colored compounds and optical isomers, including natural and synthetic optical isomers. For example, the methods and apparatus disclosed herein have applications relating to the measurement or detection of anabolic steroids and steroidal products in test samples, as well as in the measurement of a wide variety of lipoproteins and proteins in general. The following discussion first considers the inventive methods herein disclosed and concludes with a discussion of novel apparatus, which are particularly useful in performing the methods herein disclosed.

METHODS

1. Direct Detection of Cholesterol Fractions Using CD Absorption And/Or Spectrophotometric Absorption

A. Direct Detection Using CD

There are several advantages associated with the present invention which enable one skilled in the art to measure the low density cholesterol fractions in a direct manner with excellent precision. One of these advantages is the introduction of color reaction described in the literature as the Chugaev reaction (12).

The reagents utilized in the Chugaev reaction are 20% w/v $ZnCl_2$ in glacial acetic acid, and 98% acetyl chloride. They can be stored in separate containers and will remain stable for many weeks, when stored at about 40° C. Moreover, the degree of their dryness does not have to be carefully controlled. The product of their reaction is a conjugated triene CD-active derivative of cholesterol which is reddish-orange in color. This is an improvement over presently known methods, wherein the colored species are secondary dyes and not cholesterol derivatives, and their intensities are only proportional to the original cholesterol concentration.

If desired, the reactants for the Chugaev reaction may also be stored together in a ratio of about a 1:1 to 4:1 ratio of $ZnCl_2$ in glacial acetic acid to 98% acetyl chloride, when stored under airtight conditions in an amber glass, teflon or a similar container. In this regard, an extended period of stability against discoloration was observed for reactants stored together at 40° C. in amber bottles for at least 4 weeks.

With regard to the above ratios of reactants, it is further noted, that while acetyl chloride is critical to making the Chugaev color reaction proceed in a reasonably short period of time ($\approx 8$ min.), the upper volume of acetyl chloride used is not as critical as the lower volume used For example, while it is thought that the amount of acetyl chloride must be greater than 0.5 ml per 2.0 ml aliquot of the zinc chloride; spectral data have been obtained which are essentially the same when either 0.75 ml or 1.0 ml of acetyl chloride was mixed with a 2 ml aliquot of the zinc chloride.

When Chugaev reactants are used in the present invention, agents such as $Na_2SO_4$ may be added to the reactant solutions in an amount of about 1-2% w/v, in order to dry the solutions out (remove water) and air stabilize the same. However, the addition of the $Na_2SO_4$ changes the CD and absorption curves obtained for the sample. Specifically, the CD and absorption curves shift and change so that over the range of about 240 to 625 nm, a single CD peak for HDL-C occurs at about 475–480 nm. This is different from the situation with no $Na_2SO_4$ added, wherein the amount of HDL-C can be calculated from a negative peak occurring at about 390 nm and/or a positive peak at about 475 nm, or preferably the algebraic sum of the two peaks.

A second advantage of the present invention is its use of circular dichroism in a detection method for cholesterol, since CD allows for greater specificity and greater selectivity with respect to the different cholesterol subfractions than to spectrophotometric methods previously known in the art.

Figure 1:
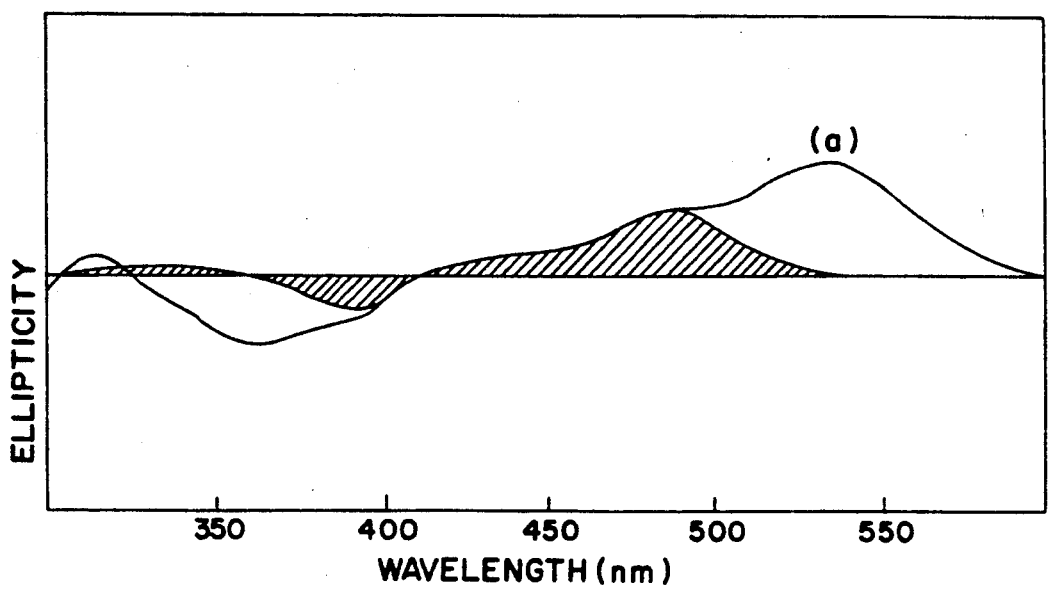
FIG. 1 is a full CD spectrum for the optically active colored product obtained from the reaction of Chugaev reagents with cholesterol. Curve (a) is representative of the total cholesterol, while the shaded area is the spectrum after the addition of the LDL precipitating agent and is therefore representative of the HDL fraction only.

In CD, a specimen is illuminated by two circularly polarized beams of light, which are travelling in unison and are polarized in opposite direction. Both beams pass through the specimen simultaneously and are absorbed. If the specimen is optically active, the beams are absorbed to different extents. The differences are displayed as a function of the wavelength of the incident light beam as a CD spectrum. No difference is observed for optically inactive absorbers so these are not detected The technique is fully described in the literature (1) as are typical CD apparatuses. The full CD spectrum for the orange colored optically active product from the Chugaev reaction with cholesterol is shown in FIG. 1. The sample is a chloroform solution of the NBS Cholesterol Standard Reference Material (SRM911a). This spectrum is used as the reference standard for all subsequent serum cholesterol measurements.

Exemplary of the advantages to using the Chugaev reaction with CD detection over previously known spectrophotometric absorption methods include the following:

(i) the CD spectra are the same whether the cholesterol is present in the test sample as the free sterol or as a fatty acid ester, so enzymatic saponification of the ester is an unnecessary step;

(ii) there is no interference from hemolyzed blood cells because the red pigments are not optically active and are therefore transparent to the CD detector;

(iii) very high triglyceride levels do not interfere either with the reaction or with the detection;

(iv) the CD spectrum is unique to cholesterol so the detection is highly selective;

(v) the reference spectrum is measured for a primary standard material, namely the purest form of cholesterol available, and not for a secondary calibrator standard;

(vi) the color is very stable because in CD detection an absorbance difference is measured, so even if the color loses intensity with time, the difference remains virtually constant;

(vii) no enzymes are involved in the color producing step and the Chugaev reagents are both stable and inexpensive.

More important than any of these advantages, is the fact, that the HDL-C and the (VLDL+LDL)-C fractions are associated with different bands in the CD absorption spectrum and can be measured directly from the same specimen, FIG. 1, without the need for a precipitation step to determine HDL-C. In this regard, measurements at 525 nm give results for the combined (VLDL+LDL)-C fractions and measurements at 390 nm (or preferably the algebraic sum of the negative and positive CD absorption peaks at 390 nm and 475 nm, respectively) give results for the HDL-C fraction It is thought preferable to determine the algebraic sum of the CD absorption peak heights at about 390 and 475 nm, when determining HDL-C levels, since this method uniformly provides a lower coefficient of variation with respect to the values obtained for HDL-C, versus the method wherein only the CD absorption measurement at about 390 nm is used. The decrease in variation with the former method results from the fact that the effects of baseline drift are lessened when the algebraic sum of the two peaks is calculated.

Based upon the above considerations, it is submitted that unlike previous methods in use, the results obtained with the present inventive methods, wherein CD is utilized, always provide measurements of low and high density fractions that are most precise and less variable than other currently known methods.

In FIG. 1, band assignments were made by comparing CD spectrum for the total cholesterol, curve (a) in FIG. 1, with the spectrum for the same sample after the selective precipitation of the low density lipid fractions with phosphotungstate-Mg, i.e., the shaded area in FIG. 1. The 525 nm band maximum was calibrated using NBS cholesterol (SRM 911a). Calibration of the 390 nm maximum was done using secondary HDL-C calibrators supplied by Sigma Chemical Co.

As an example of carrying out one of the methods of the present invention and determining the amounts of cholesterol fractions in a test sample, there is provided the following:

(a) Calibration of the CD instrument: a 50 μL aliquot of a $5\times10^{-3}$ M solution of (SRM 911a) cholesterol in AR grade chloroform is placed in a vial of 10 mL total volume. 2.00 mL of the zinc chloride reagent are added and the mixture carefully shaken. 1.00 mL of acetyl chloride is added with care, the mixture shaken, and the vial capped and incubated at 67° C. for 8 minutes. The vial is removed, cooled quickly under water. Chloroform (1.00 mL chloroform) is then added to increase the solution volume in the vial. Such an addition of chloroform may be deleted if desired, or alternatively, an appropriate solvent substituted therefor. The solution is next transferred to a 1 cm pathlength cuvette and the CD spectrum run from 625-325 nm. The spectrum is corrected on a daily basis for the cell blank and the instrument baseline by subtracting the spectrum for the reactant mixture alone.

(b) Calibration of the CD Spectra: the procedure in (a) repeated for a number of solution concentrations chosen to coincide with the typical range of serum cholesterol levels in the test sample. From the resultant calibration curve the proportionality constant relating the signal size at 525 nm to the (VLDL+LDL)-C level is 1.62 millidegrees per 100 mg/dL. The calibration at 390 nm was done in the same way, but the pure cholesterol was substituted by Sigma HDL-C calibrators The signal size to HDL-C level at 390 nm is 2.08 millidegrees per 100 mg/dL.

(c) Cholesterol Determination in Clinical Test Samples by CD: the procedure in (a) is repeated for 50 μL aliquots of serum. Before being transferred to the cuvette, the specimen is centrifuged at high speed for 2 minutes. The (VLDL+LDL)-C fraction is calculated from the measured signal height at 525 nm and the HDL-C fraction from the signal height at 390 nm. Their sum gives the total cholesterol in the specimen. Selective precipitation of the low density fraction in order to measure the HDL-C fraction is not necessary in routine measurements. It is possible therefore, to do a cholesterol-lipid profile with a volume as little as a finger stick, and get the best precision yet obtained in the measurement of low density lipid fractions.

It should be noted that the reagents can be added either in the order indicated in (a) Calibration of the Instrument; however, they can also be added simultaneously as a premixed solution or they can be added in the reverse order, e.g. add the acetyl chloride first, followed by the $ZnCl_2$ reagent. The latter mode of reagent addition had the unexpected effect of reducing the amount of precipitation in the test sample, thereby greatly reducing the scattering of incident light and thereby simplifying the subsequent measurement of absorption either by CD or by conventional spectroscopic absorption.

The value for total cholesterol obtained by summing the values for the VLDL-C+LDL-C and HDL-C subfractions, as above described, may be compared if so desired with a value obtained for total cholesterol utilizing the spectrophotometric absorption methods disclosed herein. Such a comparison can aid as a quality control check since two different methods are being used to determine total cholesterol.

Figure 2:
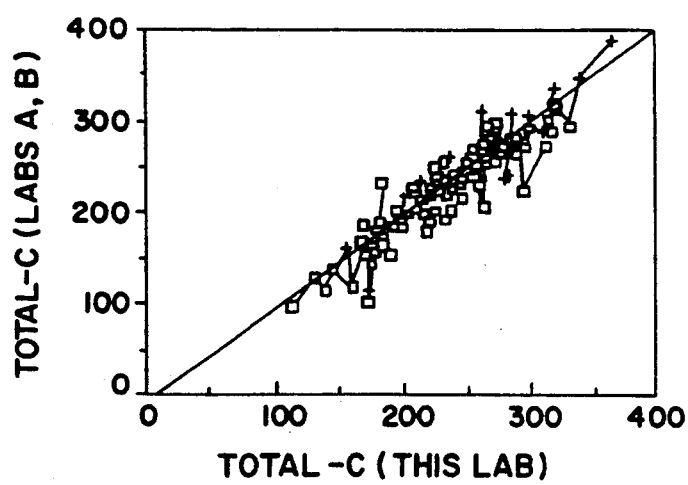
FIG. 2 represents the correlation between total cholesterol as measured in serum samples two different labs using prior art processes (Labs A and B), versus total cholesterol as measured by the method of the present invention (This Lab); $y = -10.209 + 1.0055x$, $R \wedge 2 = 0.835$.

Results of Exploratory Work: Cholesterol determinations were made on serum samples provided by two different laboratories, which employ the commercial absorption methods developed by Abbott Laboratories (Lab and DuPont (Lab B), respectively. The correlations for total cholesterol levels are excellent, FIG. 2, and well within the limits imposed by the LSP.

Figure 3A:
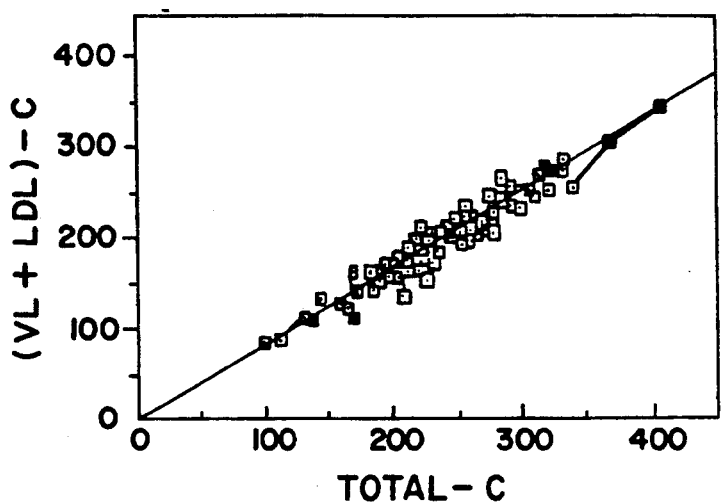
FIG. 3(a) is a graph of TC vs. (VL+LDL)-C using a method of the present invention (this lab); $y = 5.0554 + 0.84693x$, $R \wedge 2 = 0.932$.
Figure 3B:
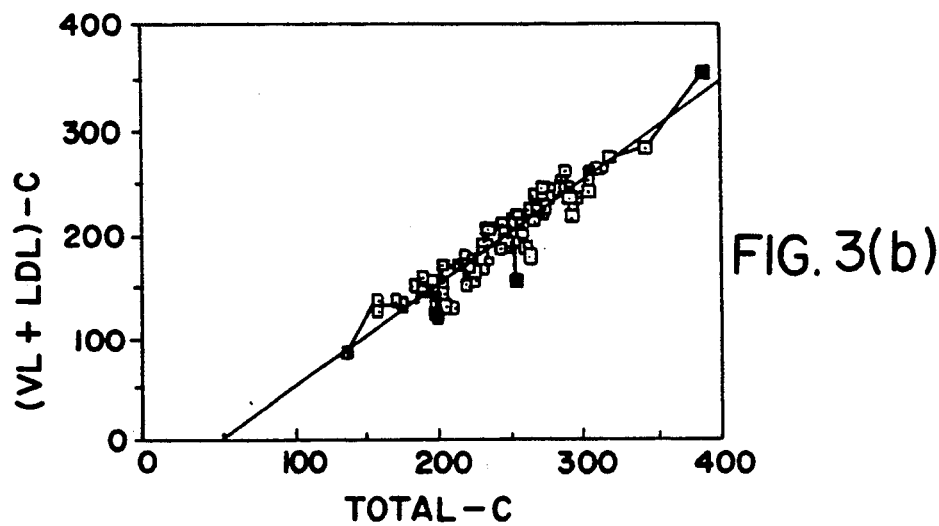
FIG. 3(b) is a graph of TC vs. (VLDL+LDL)-C using a prior art process (LAB-A); $y = 47.672 + 0.98751x$, $R \wedge 2 = 0.987$.
Figure 3C:
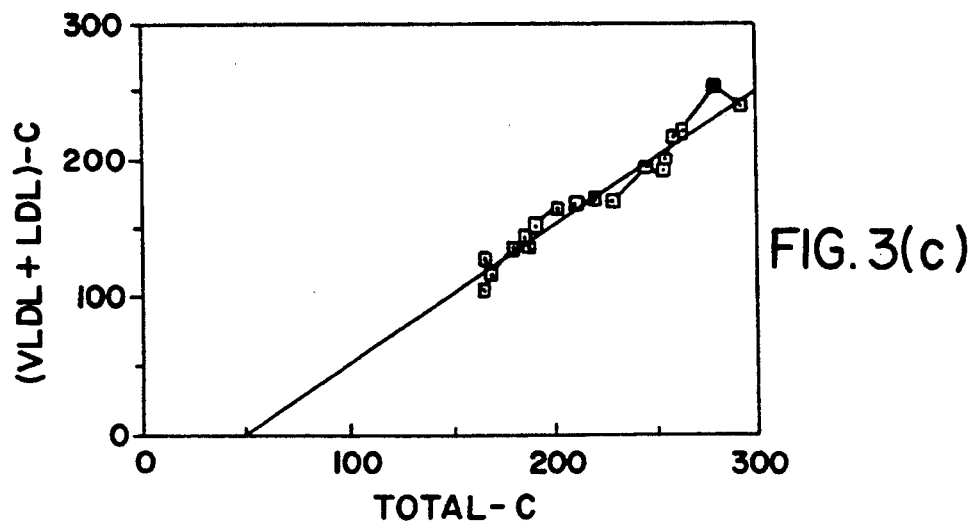
FIG. 3(c) is a graph of TC vs. (VLDL+LDL)-C using a prior art process (LAB-B); $y = -46.5222 + 0.9869x$, $R = 0.98$.
Figure 4A:
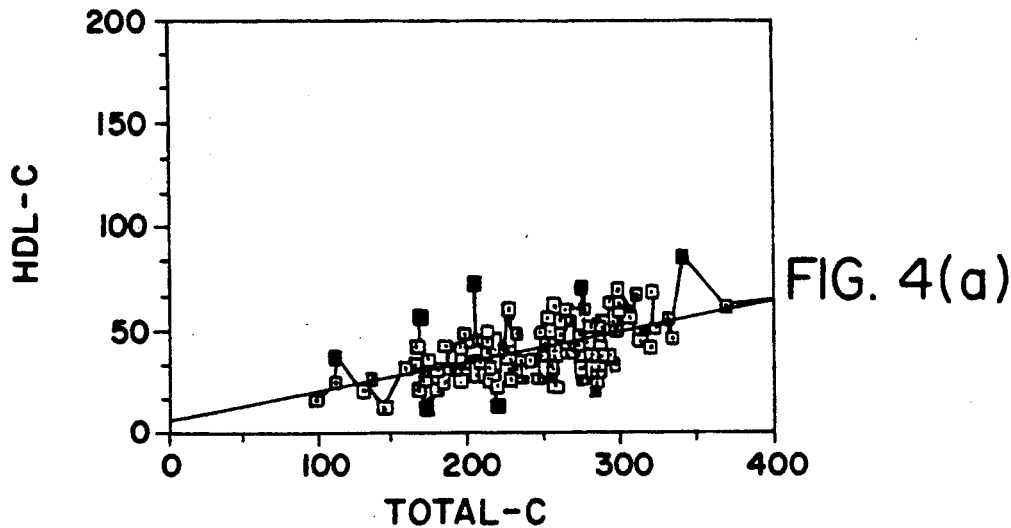
FIG. 4(a) is a graph of TC vs. HDL-C using the method of the present invention (this lab); $y = 5.2861 + 0.14995x$, $R \wedge 2 = 0.335$.
Figure 4B:
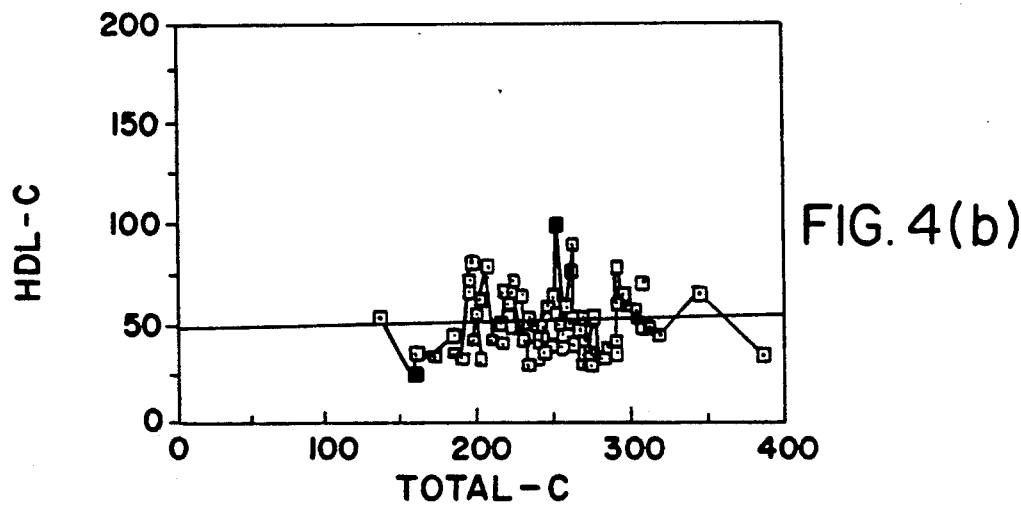
FIG. 4(b) is a graph of TC vs. HDL-C using a prior art process (LAB-A); $y = 47.648 + 0.012569x$, $R \wedge 2 = 0.001$.
Figure 4C:
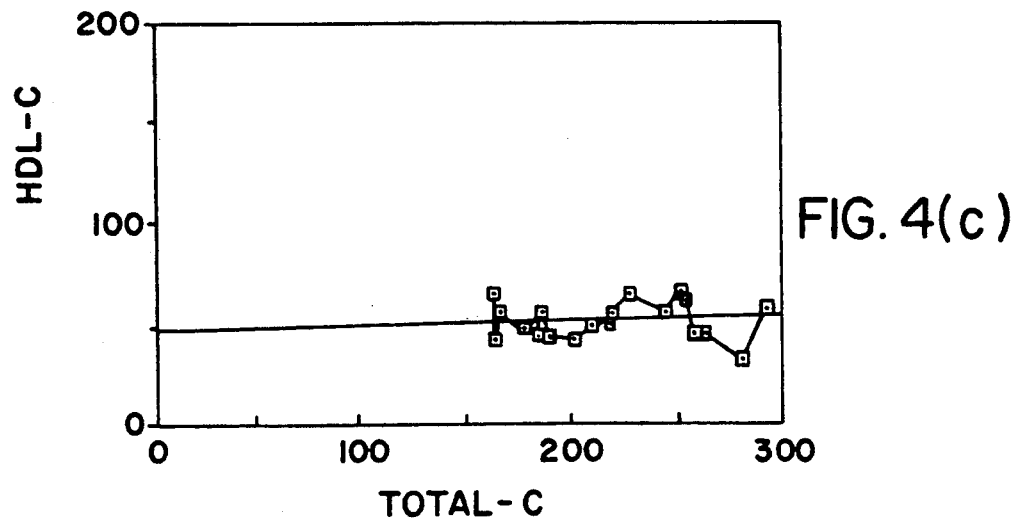
FIG. 4(c) is a graph of TC vs. HDL-C using a prior art process (LAB-B); $y = 46.522 + 0.0131x$, $R = 0.06$.

A good case for believing that this new method is an improvement over prior methods, is to compare the correlations for the three data sets treated independently. Plots of total cholesterol versus (VLDL+LDL)-C are linear in every case, but there is a bias of almost 50 mg/dL in the intercepts on the x-axis for both absorption methods, FIGS. 3(b) and 3(c) and zero correlation between the total and HDL-C data for these same data sets, FIGS. 4(b) and 4(c). The Chugaev-CD data correlations by comparison, are excellent with low correlation intercepts, FIGS. 3(a) and 4(a), and the correlation slopes indicate that, for these sample populations, the "average" percentages for the HDL-C and (VLDL+LDL)-C fractions are 15% and 85%, respectively, which are in good agreement with the values normally accepted as typical for human serum distributions based upon ultracentrifugation data. Correlation slopes for the previously known spectrophotometric absorption methods are both one, which is not possible, and which arises because a virtually constant measured value of 50 mg/dL for HDL-C is subtracted from measured TC values to obtain the results for (VLDL+LDL)-C.

Accuracy and Analysis Time: Since there are no commercial reference standards for either LDL-C or VLDL-C, the accuracy cannot be evaluated. However, the precision and repeatability in the (VLDL+LDL)-C measurements are better than ±2%. With this level of precision, the confidence in one's ability to correlate the changes in LDL-serum cholesterol in reduction therapy studies, which involve diet and/or exercise modifications, is meaningfully improved.

The approximate time for a single analysis by the Chugaev-CD method with CD detection is 15 minutes. While this is long compared to the commercial absorption methods used only for TC measurements, results for both low and high density fractions are obtained simultaneously. Thus, total time required for a complete cholesterol analysis, including measurement of sub-fractions by CD, is less than that required with the use of prior methods. Because of the stability of the color, the turn around time can be reduced considerably by incubating several samples at once. With greater incident light intensities, sample path lengths can be reduced from 1 cm and the measurements can be automated. Such a procedure, it is fully expected, would then be time competitive with present methods, (which do not possess the selectivity and sensitivity of the present inventive methods which utilize CD).

Utilizing Chugaev reactants in procedures such as those provided above, several National Bureau of Standards SRM total cholesterol standards were also examined. The three samples tested were listed in the NBS catalogue as (1951-1)(210.36±2.46 mg/dL total), (1951-2)(242.29±1.53 mg/dL total), and (1951-3)(281.97±1.83 mg/dL total). According to the NBS Certificate of Analysis, the serum was donated by the CDC. The figures in parentheses are those measured at NBS and they compare extremely well with the CDC determinations using the modified Abell-Kendall method. The figures that we obtained from the Chugaev, by adding the CD absorption values for the two fractions (HDL-C and VLD-C+LDL-C) were 206 mg/dL, 241.1 mg/dL, and 286.6 g/dL, respectively. These results clearly evidence the effectiveness of the present inventive methods in determining cholesterol levels directly and precisely.

B. Direct Detection Using Spectrophotometric Absorption

As noted above, the addition of substances to dry and stabilize the Chugaev reagent resulted in unexpected changes in the CD spectrum of the test samples. In this regard, it should be noted that the optically active colored product of the Chugaev reactions with cholesterol in the test samples has an absorption spectrum that extends over the range of about 240–700 nm [FIG. 7, Absorption Curve (a)]. It shows a strong absorption maximum at about 525 nm, which is associated with and proportional to the total cholesterol (TC) in the sample. Provided there are no strong interferences from the red pigments of hemolyzed blood cells, absorbance measurements at 525 nm can be used to determine TC. Calibration data from measurements at 525 nm suggest a molar absorptivity for the colored product to be on the order of about 13,500.

Without the presence of special additives in the Chugaev reagent, there are no indications of selective absorbances by the separate subfractions of the cholesterol in the test samples. The addition of 1-2% w/v anhydrous $Na_2SO_4$ to the basic Chugaev reagent produces a radical change in the absorption spectrum. Specifically, the strong absorption peak at 525 nm is lost and a peak of smaller intensity and an absorption maximum of about 480 nm is revealed [FIG. 7, Absorption Curve (b)]. A similar effect is produced by other additives, namely alkali metal sulfates, alkaline earth metal sulfates and concentrated $H_2SO_4$ in an amount of about 1 to 2% W/v, or small amounts of concentrated $H_2SO_4$. Transitional metal sulfates also showed this effect, however they formed colored solutions and, for that reason, are not the preferred choice. Comparisons between the CD spectral data of clinical samples and commercial preparations available from Sigma Biochemical suggest that this 480 nm peak correlates with HDL-C. Figures suggest a molar absorptivity for the 480 nm peak to be on the order of about 4,000. In the absence of additives to the Chugaev reagent, there is a small contribution from this peak to the major absorption band under the 525 nm peak. Therefore, the difference between the optical densities (i.e. with and without sulfate additive), measured at 525 nm, is proportional to the sum of the combined VLDL-C+LDL-C subfractions.

Other additives, namely precipitating agents such as dextran sulfate and alkali metal perchlorates such as sodium perchlorate in an amount of about 1 to 2% v/W alter the absorption spectrum as shown in FIG. 7 [Absorption Curve (c)]. Studies indicate that this peak, with a maximum absorption at about 500 nm, correlates with the combined LDL-C+VLDL-C subfraction. Thus, there is evidence to suggest that the band that remains after the addition of the metal perchlorates can be used to discriminate between the VLDL-C and the LDL-C subfractions, so that the amounts of these two sub-fractions can also be determined.

To reiterate, using a measurement at about 525 nm for the product of the basic Chugaev reagent and a measurement at about 480 nm for the product of the Chugaev reagent with an appropriate sulfate, such as taught herein, values can be obtained directly for TC and HDL-C, respectively. Differences in absorption at about 525 nm (with sulfate additives versus without sulfate additives) gives values for combined VLDL-C+LDL-C. Separation of VLDL-C and LDL-C is possible from a third measurement made at about 500 nm after reaction with a Chugaev/perchlorate reagent(s), such as taught herein. Spectrophotometric methods herein encompassed can utilize each of these measurement techniques if so desired.

It should also be noted that since the intensity of the band attributed to HDL-C is on the order of one half the intensity of the TC spectrum at about 480 nm, it is conceivable that a mathematical algorithm can be written to curve-fit the spectrum for total cholesterol obtained from the basic Chugaev reagents (between about 400–700 nm) with weighted averages of the spectra for the three subfractions As such, it may be possible to carry out the cholesterol lipid analysis to be done using only the spectrum from the colored product of the reaction of cholesterol in the clinical sample with the basic Chugaev test reagent.

The above described spectrophotometric absorption reactions do not require the use of a CD instrument, yet they offer similar opportunity for simultaneous, on-line detection of cholesterol and cholesterol subfractions in clinical samples. The use of spectrophotometric absorption methods using such Chugaev reaction reagents also permits much greater sensitivity than the CD methods herein disclosed allow for, since only a very small portion of the incident light can be used for CD signal generation. As such, the spectrophotometric absorption methods herein disclosed permit the use of smaller volumes of sample, thereby reducing possible interferences caused by other materials and the total amount of precipitates formed by the reaction. Conversely, however, these reactions are more susceptible than CD to interferences from pigments released by hemolysis of the blood samples. Finally, it is important to note that, as with the CD studies mentioned above, addition of the acetyl chloride to the sample first, followed by addition of the ZnCl/acetic acid reagents reduces even further the interferences caused by precipitation of the clinical sample. Indeed it is possible to carry out spectrophotometric absorbance reactions for this application using whole blood samples.

Based on the above considerations, there is provided herein a novel spectrophotometric absorption detection method, wherein reagents are reacted with cholesterol in clinical samples so that a direct measurement of cholesterol subfractions can be made. The measurements can be made either as a full spectrum over the range of about 400–700 nm or at two or more selected wavelengths, namely about 480 nm for HDL-C, 500 nm for VLDL-C, and 525 nm for combined VLDL-C+LDL-C (or TC, as desired) using additives as herein taught. The major procedural difference between the absorption and the CD method relates to the standards used. While cholesterol itself can be used as a standard for the CD reactions, clinical standards for TC and cholesterol subfractions obtained from the CDC, CAP or commercial sources must be used to calibrate the absorption spectrometer.

2. Indirect Detection of Cholesterol Fractions (Through Associated Lipoproteins) using CD Using CD techniques similar to those disclosed above, except by utilizing a novel bilirubin conjugate reagent (instead of a Chugaev reagent), buffered at about 5.0 to 5.1, one can measure the levels of HDL-C in serum indirectly. This is done by directly determining the serum levels of one or more different lipoproteins or apoliproproteins associated with the HDL-C fraction. In this regard, lipoproteins associated with the VLDL-C+LDL-C fraction are usually designated beta lipoproteins and include B-100 C and E apliproproteins, while lipoproteins associated with the HDL-C fraction are designated alpha lipoproteins and include A-1, A-11, C, D and E apoliproproteins. The bilirubin conjugates which are formed with the HDL-C associated lipoproteins or apoliproproteins are measured directly with the method, and the amount of HDL-C in the serum is proportionate to the amount of lipoprotein or apoliproprotein measured.

Specific comments relating to the above bilirubin conjugate methodology as pertain to determining the presence of alpha lipoproteins in a sample are as follows. However, the same are not limited to the present invention, since similar techniques (e.g., using a bilirubin conjugate reagent buffered to a pH of about 5.0–5.2), as may be seen below, can be useful in measuring the amounts of various proteins or lipoproteins present in a serum sample.

Bilirubin Absorption Test for Alpha-Lipoprotein

Bilirubin is known to bind to serum proteins and has actually been assayed using CD detection (2), after being bound to human serum albumin (HSA). Bilirubin is not, by itself, CD active. Because of the peptide link chromophore, HSA is CD active in the far UV (maxima around 218 nm). Together in aqueous solution, the molecules form a strong association complex that absorbs and is CD active in the visible range of the spectrum. The color of the solution is not noticeably changed from that of the free bilirubin solution and the absorption spectrum of the free bilirubin and the HSA-complexed bilirubin differ only slightly. The change is too small to enable the clinical assay of either HSA or bilirubin using absorption detection. Only the complexed form has a CD spectrum and by carefully controlling the conditions, either molecule can be a reagent suitable for the assay of the other.

Bilirubin (and/or other organic dyestuffs) has the potential to bind to all the serum proteins HSA is the preferred host, because it is present in very large molar excess over all other proteins. I have envisioned that a detector selective enough to discriminate among the various bilirubin-protein complexes might be developed for protein recognition and for profiling serum proteins, and that full spectrum CD detection might have a significant degree of selectivity to accomplish this task. In this regard, preliminary evidence suggests that different CD spectra exist for bovine serum albumin (BSA), HSA, and gamma-globulins (GG).

Figure 5B:
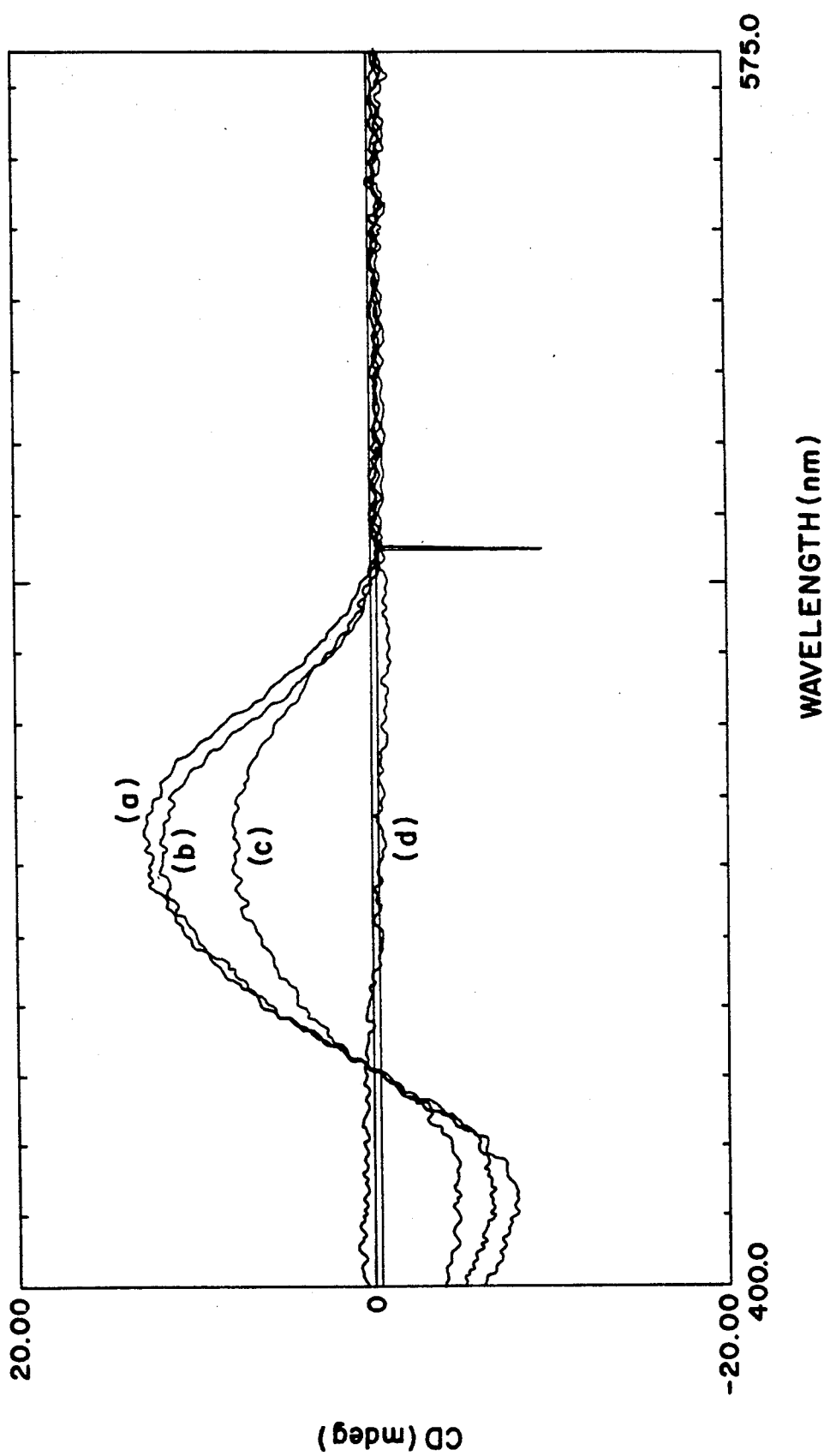
FIG. 5(b) is a graph that shows the further pH dependence of the CD spectrum of the Human Serum Albumin+ Bilirubin conjugate; Curve (a)=pH 8.2; Curve (b)=pH 7.4; Curve (c)=pH 9.8; and Curve (d)=pH 5.00.
Figure 6:
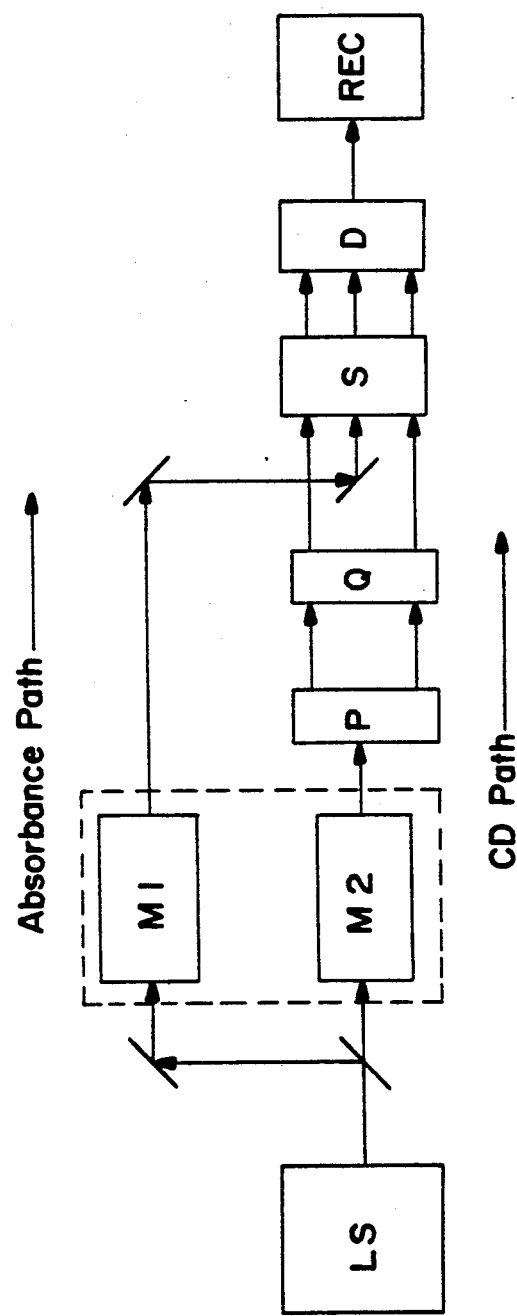

The CD spectrum of the HSA-bilirubin complex is typically bi-modal and has a strong pH dependence, with each band reversing polarity as the pH is increased, FIG. 5(a). At pH 5.0–5.2, roughly the center of the range around the isoelectric point for HSA, the CD spectrum is virtually baseline. Proteins with slightly different isoelectric ranges might become preferred hosts for bilirubin in the 5.0–5.2 pH range. With this thought in mind, bilirubin conjugate was added to specimens of human serum and the CD spectra were measured as a function of pH. As expected, the dominant spectrum at most buffered pH values, was that for HSA-bilirubin complex, verified by checking it against an HSA standard (Sigma). The spectrum at pH 5.0, however, is not typical of HSA, FIG. 5(b), nor does it correspond with the spectrum for the GG-bilirubin complex.

A standardized procedure was developed to obtain reproducible spectra for a given serum. The details are as follows: to 200 $\mu$L of serum in a 10 mL vial, add 3.0 mL of pH 5.0 buffer and 50 $\mu$L of a $1 \times 10^{-3}$ M (7 mg/10 mL water) solution of bilirubin conjugate (Porphyrin Products Inc., Logan, Utah). Shake and allow to stand for 5 minutes. Transfer the solution to a 1 cm path-length, 3 mL total volume, spectrophotometric cuvette and run the CD spectrum from about 575 to 375 nm. The bilirubin stock solution must be prepared using distilled water and not pH 5.0 buffer, in which it rapidly oxidizes to biliverdin. The stock in water is sufficiently stable for several hours, but not overnight ($\approx$ 16 hours).

Spectra, run for several serum samples, show a broad general similarity, but subtle changes are observed in the slope and in the crossover points (i.e., wavelengths at which the CD signal is zero). Signal intensities measured at 495 nm, varied from sample to sample, implying a dependence of the signal height upon the serum content of whatever protein was the preferred host.

The alpha-lipoprotein fraction from the ISOLAB ® separator (a heparin-agarose column), when reacted with bilirubin conjugate at a pH 5.0, was found to give a CD spectrum analogous to that for the complex with the anonymous "serum protein(s)". The implication was that the serum constituent that binds with bilirubin at pH 5.0, is the alpha lipoprotein, i.e., that associated with HDL-cholesterol. The analogous spectrum was also observed for the bilirubin complex of HDL-cholesterol standard solutions obtained from Sigma Chemical Co. Preliminary measurements made for small number of serum samples do in fact indicate a correlation between the signal height at 495 nm for the complex and the HDL-cholesterol contents measured by the Chugaev method.

Based upon the above considerations, it is thought that using the above techniques, one may measure the amount of alpha-lipoprotein in a serum test sample, the indicated lipoprotein amount being proportional to the amount of HDL-C present in the sample. The technique can also have application in the measurement of a large variety of proteins in almost any test sample, such proteins including, but not being limited proteins, urinary proteins, food proteins, and the like.

In order to further evidence the effectiveness of the present inventive methods in determining cholesterol subfraction or cholesterol associated alpha lipoprotein serum levels, the following experimental data are provided in Table 1.

TABLE 1

| Patient | Blood Fractions | | | |
|---|---|---|---|---|
| | VL + LDL (Chug)[1] | HDL (Chug)[2] | HDL (BR)[3] | HDL (enz)[4] |
| A | 126 | 31 | 28 | [63] |
| B | 165 | 28 | 25 | [46] |
| C | 220 | 33 | 28 | — |
| D | 237 | 34 | 41 | [55] |
| E | 199 | 29 | [64] | 32 |
| F | 188 | 39 | 40 | 36 |
| G | 249 | 36 | 36 | 43 |
| H | 199 | 34 | 31 | 25 |
| I | 144 | 28 | 28 | [53] |
| J | 216 | 46 | [29] | 52 |
| K | 190 | 38 | 34 | 35 |
| L | 211 | 41 | 29 | — |
| M | 239 | 39 | 31 | — |
| N | 190 | 39 | 26 | [56] |
| O | 220 | 50 | 41 | — |
| P | 174 | 46 | [24] | 46 |
| Q | 249 | 51 | [36] | 57 |
| Q* | 242 | 48 | — | — |
| R | 184 | 47 | 36 | [60] |
| S | 205 | 29 | [46] | 33 |
| T | 126 | 46 | 37 | 45 |
| U | 157 | 46 | 52 | 49 |
| U* | 163 | 41 | — | — |
| V | 94 | 31 | 37 | [86] |
| W | 293 | 38 | 46 | — |
| X | 239 | 47 | — | [84] |
| Y | 207 | 57 | — | 55 |
| Sigma 400 | 340 | 61 | — | — |

TABLE 1-continued

| Patient | Blood Fractions | | | |
|---|---|---|---|---|
| | VL + LDL (Chug)[1] | HDL (Chug)[2] | HDL (BR)[3] | HDL (enz)[4] |
| Sigma H | 230 | 52 | — | — |

[1] VL + LDL (Chug) - Cholesterol subfraction VLDL-C + LDL-C using Chugaev reagents and taking CD absorption measurement at 575 nm.
[2] HDL (Chug) - Cholesterol subfraction HDL-C obtained using Chugaev reagents and taking algebraic sum of CD absorption measurements at 390 and 475 nm.
[3] HDL (BR) - subfraction HDL-C obtained using bilirubin conjugate at pH 5.0 and measuring directly the alpha lipoproteins associated with the HDL-C fraction, by taking CD absorption at 495 nm.
[4] HDL (enz) - subfraction HDL-C obtained using the enzymatic method designated by Lab(A) and Lab(B).
*Asterisk indicates test was performed on patient's serum using mixed Chugaev reagents stored 4 weeks at 40° C..
[] = brakcets indicate HDL measurements which are substantially different from HDL measurements using other methods.

Of the experimental results shown in Table 1, it is noted that 12 out of 20 values for each of the HDL-C(Chug) and HDL-C(enz) methods are within 10 mg/dL, and that 16 of the 23 values for HDL-C(BR) are within 10 mg/dL. Such results clearly help to evidence the accuracy of the present methods.

Inventive Apparatus

Upon review of the above methods section, it can be easily ascertained that the present inventive methods have many advantageous attributes when compared with presently known methods for determining cholesterol levels, detecting steroids, etc. in test samples. However, the present invention also encompasses novel instruments, which can allow one skilled in the art to markedly increase the speed with which the present inventive methods can be performed. Such inventive instruments are outlines above (see Section entitled "Summary of the Invention").

In general, each of the novel inventive instruments outlined above, can allow one to decrease turnaround time on a serum test sample by utilizing the fact that TC=VLDL-C+LDL-C+HDL-C (Equation I), and that it is possible to construct instruments, wherein CD and spectrophotometric absorption measurements at identical or different wavelengths are performed simultaneously, if desired.

For example, one of the detection instruments encompassed hereby can simultaneously, if desired, measure HDL-C by CD absorption at a first wavelength (at about 390 nm) and/or a first and a second wavelength (preferably about 390 and 475 nm), and simultaneously if desired, measure LDL-C+VLDL-C by CD absorption at a third wavelength (preferably at about 525 nm). TC can then be determined indirectly by computer/calculator means by summation of the amounts of the cholesterol subfractions already determined. Means for preparing such an instrument would include those means generally known in the art for preparing CD instruments. Such an instrument may include separate detector systems for detecting CD absorbance or spectrophotometric absorption at each different wavelength monitored, if so desired.

In another detection instrument encompassed hereby, absorption measurements, both spectrophotometric and CD, are made at a single wavelength to determine the levels of TC and LDL-C+VLDL-C, respectively present. In such a system, two separate detector systems (one for spectrophotometric absorbance and one for CD absorbance) may be used, if so desired. It is thought preferable, however, to utilize a switching device in such an instrument which allows one to change from the CD detection mode of operation to the spectrophotometric absorption detection mode, since the two absorption measurements are taken at a single wavelength, and as such, time factors are not thought to be increased significantly by utilizing switching devices.

If desired, an instrument encompassed hereby can also be constructed which contains three separate detector systems, which may be used as part of a means for simultaneously monitoring the absorbance of the three different cholesterol levels in a test sample, (spectrophotometric or CD detectors system), i.e., HDL-C, VLDL-C+LDL-C (CD detector system) and TC (Spectrophotometric detector system). However, again it is noted that switching device(s) can advantageously be utilized to switch between the CD mode(s) of operation and/or the spectrophotometric mode(s) of operation. The use of such switching device(s) is thought preferable in such an instrument.

Of the novel CD instruments outline above, it is thought that instruments wherein the HDL-C and either TC or VLDL-C+LDL-C are directly measured (and, conversely, VLDL-C+LDL-C or TC are computed) are the most advantageous to utilize, since such instruments only require that two cholesterol levels be determined directly, while the third cholesterol level is determined based upon Equation I above. For absorption spectrometry it is thought preferable, for the same reasons as outlined above, to use an instrument wherein the TC and HDL-C are determined directly, while LDL-C+VLDL-C are computed. In the same manner, instruments referred to herein which require that three separate cholesterol levels to be determined directly without making use of Equation I above, are thought less preferred. Nonetheless, it is noted that whenever two different methods are available to make independent cholesterol measurements, this can aid as a quality control check for the clinical measurement. For such reasons, each of the inventive detection instruments herein disclosed are thought advantageous to utilize in the present inventive methods.

Yet another instrument encompassed hereby can be a spectrophotometric instrument having no CD capability. Such an instrument should be equipped with detectors capable of measuring the absorption of the colored products of the Chugaev reagent over a range of from about 400-700 nm (preferably about 450-625 nm), or at discrete points such as at about 525 nm and 480 nm and, possibly, at about 500 nm. If automated, it should also have the capability of adding the Chugaev reagents in the order described above to reduce precipitation. Further, if an automated instrument is used, it should preferably have the means either to add the Chugaev reagents, with or without additives to separate sample containers for analysis or to add sequentially the basic Chugaev reagent followed by the additive(s) to the same sample container, thereby permitting on-line determination of both TC and HDL-C simultaneously or in sequence. Finally, any such absorption spectrometer, manual or automatic, should preferably have the means to determine the levels of LDL-C+VLDL-C in a test sample by a calculation or computation from the TC and HDL-C values. It may also have the means to determine VLDL-C at about 500 nm as described above and to use that value in the computation of LDL-C in the clinical sample.

With spectrophotometric absorption devices such as those disclosed above, the TC level in a test sample could be read directly and the HDL-C level read directly after addition of an appropriate sulfate, with absorption readings being done simultaneously in two separate cuvettes after adding the basic Chugaev reagents to one tube and the basic Chugaev reagents plus sulfate additive to the second tube. There could also be used with such devices a sequential process in which the basic Chugaev reaction reagents are added to a test sample in a cuvette, taking an absorption reading of the sample, then adding an appropriate sulfate additive to the tube and taking a second absorption reading of the sample. Combined VLDL-C+LDL-C could then be calculated or computed automatically from the two absorption reading, if so desired.

With spectrophotometric absorption devices such as those disclosed above, one could also determine TC, HDL-C and VLDL-C level directly. In such a procedure test sample, having the basic Chugaev reagents added thereto would be in at least a first and a second cuvettes (or tubes) and a spectrophotometric absorption reading of one of the samples taken. Thereafter, an appropriate sulfate additive would be added to the sample in the first cuvette and an appropriate perchlorate (or dextran sulfate) added to the sample in the second cuvette, and a spectrophotometric absorption reading made of the test sample in each cuvette. The level of LDL-C in the sample could then be automatically calculated from the three absorption readings, if so desired.

It is also noted, that instruments herein encompassed for performing the methods of the present invention, could be designed so that separate light trains exist for the CD and spectrophotometric absorption signals. In addition, if laser lights are utilized in such instruments, monochromators could be eliminated.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

1. Lambert, J. B., Shurvell, H. F., Verbilt, L. Cooks, R. G., and Stout, G. H., "Organic Structural Analysis", Macmillan, New York, N.Y. 1976.
2. Grahnen, A., Sjoholm, I., and Michaëlsson, M., Clinica Chimica Acia, 52, 187–196 (1974).
3. Kannel, W. B., Castelli, W. P., Gordon, T. et al., "Serum cholesterol, lipoproteins, and the risk of coronary heart disease: The Framingham Study", Ann..Intern.Med. 1971; 74:1-11.
4. Castelli, W. P., Garrison, R. J., Wilson, W. F., Abbott, R. D., Kalousdian, S., Kannel, W. B., "Incidence of coronary heart disease and lipoprotein cholesterol levels", JAMA 1986, 256:2835–2838.
5. Abbott, R. D., Garrison, R. J., Wilson, P. W. F. et al., "Joint distribution of lipoprotein cholesterol classes, The Framingham Study", Arteriosclerosis 1983, 3:260–272.
6. Laboratory Standardization Panel, NCEP, "Current status of blood cholesterol measurement in clinical laboratories of the United States, A report from the Laboratory Standardization Panel of the National Cholesterol Education Program", Clin.Chem. 1988, 34:193–201.
7. Superko, H. R., Bachorik, P. S., Wood, P. D., "High-density lipoprotein cholesterol measurements—A help or hindrance in practical clinical medicine?" JAMA 1986, 256: 2714–2717.
8. Posnick, L., "Labs now better at cholesterol tests, data show", reported in Clin.Chem.News 1989; 15(9):14.
9. Warnick, G. R., Albers, J. J., Teng-Leary, E., "HDL cholesterol:Results of interlaboratory proficiency test." Clin.Chem. 1980; 26:169–170.
10. Grundy, S. M., Goodman, D. W., Rifkind, B. M., Cleeman, J. I., "The place of HDL in cholesterol management. A perspective from the national cholesterol education program." Arch.Inter.Med. 1989; 149:505–510.
11. Purdie, N., Swallows, K. A., "Analytical applications of polarimetry, optical rotatory dispersion, and circular dichroism." Anal.Chem., 1989; 61:77A–89A.
12. Cox, R. H. and Spencer, E. Y., Can. J. Chem., 29, 217 (1951).
13. Katzung, B. G., "Basic and Clinical Pharmacology, 4th Ed.", p. 419–421, Appleton & Lange, Englewood Cliffs, N.J. (1989).

What is claimed is:

1. A clinical detection method for determining the amount of cholesterol, lipoprotein, anabolic steroid or other steroidal product present in a clinical test sample, the method comprising:
   (a) forming an optically active, colored reaction product with said cholesterol, lipoprotein, anabolic steroid or other steroidal product present in the test sample;
   (b) determining the CD absorption spectrum of said test sample over the range from about 150 nm to about 700 nm; and
   (c) determining the amount of the cholesterol, lipoprotein, anabolic steroid or other steroidal product present in the test sample based on the CD absorption of the test sample in step (b).

2. A clinical detection method as recited in claim 1, in which said optically active, colored reaction product is formed by reaction of Chugaev reagents with said cholesterol, lipoprotein, anabolic steroid or other steroidal product.

3. The clinical detection method as recited in claim 2, wherein the Chugaev reagents comprise:
   zinc chloride, glacial acetic acid and acetyl chloride.

4. The clinical detection method as recited in claim 2, wherein the Chugaev reaction product is formed by adding the following Chugaev reagents sequentially to the test sample:
   (1) acetyl chloride, and then
   (2) zinc chloride and glacial acetic acid.

5. A clinical detection method as recited in claim 1, wherein the amount of cholesterol present in a clinical test sample is determined.

6. A clinical detection method as recited in claim 5, wherein said reaction product is formed by reaction of Chugaev reagents with said cholesterol present in said test sample.

7. The clinical detection method as recited in claim 6, wherein the Chugaev reagents comprise:
   zinc chloride, glacial acetic acid and acetyl chloride.

8. The clinical detection method as recited in claim 6, wherein the Chugaev reaction product is formed by adding the following Chugaev reagents sequentially to the test sample:
   (1) acetyl chloride, and then
   (2) zinc chloride and glacial acetic acid.

9. A clinical detection method for determining the amount of cholesterol, lipoprotein, anabolic steroid or other steroidal product present in a clinical test sample, the method comprising:
   (a) forming an optically active, colored reaction product with said cholesterol, lipoprotein, anabolic steroid or other steroidal product present in the test sample;
   (b) determining the CD absorption of said test sample at one or more discrete wavelengths within a range from about 150 nm to about 700 nm; and
   (c) determining the amount of the cholesterol, lipoprotein, anabolic steroid or other steroidal product present in the test sample based on the CD absorption of the test sample in step (b).

10. A clinical detection method as recited in claim 9, in which said optically active, colored reaction product is formed by reaction of Chugaev reagents with said cholesterol, lipoprotein, anabolic steroid or other steroidal product.

11. A clinical detection method as recited in claim 10, wherein the amount of cholesterol present in a clinical test sample is determined.

12. A clinical detection method as recited in claim 10, wherein the Chugaev reagents comprise:
   zinc chloride, glacial acetic acid and acetyl chloride.

13. A clinical detection method as recited in claim 10, wherein the Chugaev reaction product is formed by adding the following Chugaev reagents sequentially to the test sample:
   (1) acetyl chloride, and then
   (2) zinc chloride and glacial acetic acid.

14. A clinical detection method as recited in claim 11, wherein said reaction product is produced by reaction of Chugaev reagents with said cholesterol present in said test sample.

15. A clinical detection method as recited in claim 11, in which a HDL-C and LDL-C+VLDL-C levels are determined by CD absorption, and a total cholesterol level is determined by summing the HDL-C and LDL-C+VLDL-C levels.

16. A clinical detection method for determining the amount of cholesterol in a test sample, as recited in claim 11, the method further comprising the step of determining the total cholesterol level by spectrophotometric absorption.

17. A clinical detection method as recited in claim 14, wherein the Chugaev reagents comprise:
   zinc chloride, glacial acetic acid and acetyl chloride.

18. The clinical detection method as recited in claim 14, wherein the Chugaev reaction product is formed by adding the following Chugaev reagents sequentially to the test sample:
   (1) acetyl chloride, and then
   (2) zinc chloride and glacial acetic acid.

19. A clinical detection method as recited in claim 16, in which a HDL-C level is determined by subtracting the level of LDL-C+VLDL-C from a total cholesterol level.

20. A clinical detection method as recited in claim 16, in which the total amount of cholesterol is determined by absorption and is compared with a total cholesterol level determined by summing LDL-C+VLDL-C and HDL-C levels.

21. The clinical detection method for determining the amount of a lipoprotein present in a clinical serum test sample, the method comprising:

(a) forming a bilirubin conjugate with the lipoprotein at a pH of about 5.0 to 5.2,
(b) determining the CD absorption of said test sample for at least one point in the range of about 375 to 575 nm, and
(c) determining the amount of the lipoprotein present in the test sample, based on the CD absorption of the test sample in step (b).

22. A clinical detection method, as recited in claim 21, wherein said lipoprotein is an alpha-lipoprotein.

23. A clinical detection method, as recited in claim 21, wherein the CD absorption of said test sample is determined at about 495 nm.

24. A clinical detection method for determining the amount of cholesterol present in a clinical test sample, the method comprising:
forming a colored reaction product with said cholesterol by reacting a Chugaev reagent with at least a portion of said test sample, determining the spectrophotometric absorption of said reaction product, and determining the amount of cholesterol present in the test sample based on the spectrophotometric absorption of the reaction product.

25. A clinical detection method as recited in claim 24, in which the colored reaction product is formed by adding the following components sequentially to the test sample to form a Chugaev reaction product:
(1) acetyl chloride, and then
(2) zinc chloride and glacial acetic acid.

26. A clinical detection method for determining the amount of a cholesterol lipoprotein subfraction present in a clinical test sample, the method comprising forming a colored reaction product with said cholesterol lipoprotein subfraction, determining the optical absorption spectrum of said reaction product, and determining the amount of the cholesterol lipoprotein subfraction present in the test sample based on the optical absorption of the reaction product;
wherein the colored reaction product is formed by performing at least one of the following steps:
(a) reacting at least a portion of said clinical test sample with a Chugaev reagent and with an additive selected from the group consisting of an alkali metal sulfate, alkali earth metal sulfate, transition metal sulfate and concentrated sulfuric acid;
(b) reacting at least a portion of said clinical test sample with a Chugaev reagent and with an additive selected from the group consisting of dextran sulfate and an alkali metal perchlorate.

27. A clinical detection method as recited in claim 26, in which the colored reaction product is formed in at least one of steps (a) and (b), by adding the following components sequentially to the test sample to form a Chugaev reaction product:
(1) acetyl chloride, and then
(2) zinc chloride and glacial acetic acid.

28. A clinical detection method as recited in claim 26 in which both steps (a) and (b) are performed.

29. A detection method as recited in claim 26, wherein:
said alkali metal sulfate is selected from the group consisting of lithium sulfate, sodium sulfate and potassium sulfate,
said transition metal sulfate is selected from the group consisting of scandium sulfate, titanium sulfate, chromium sulfate, manganese sulfate, nickel sulfate, zinc sulfate, copper sulfate and calcium sulfate, and
said alkali metal perchlorate is selected from the group consisting of lithium perchlorate, sodium perchlorate and potassium perchlorate.

30. A clinical detection method as recited in claim 27, wherein the acetyl chloride is added to the test sample before an alkali metal sulfate, alkali earth metal sulfate, transition metal sulfate, concentrated sulfuric acid, dextran sulfate or alkali metal perchlorate is added to the test sample.

31. A clinical detection method for determining the level of cholesterol and the level of at least one cholesterol lipoprotein subfraction present in a clinical test sample, the method comprising:
(a) reacting at least a portion of said clinical test sample with a Chugaev reagent mixture and measuring the spectrophotometric absorption of the resultant reaction mixture; and performing at least one of steps (b) and (c):
(b) reacting at least a portion of said clinical test sample with a Chugaev reagent and with an additive selected from the group consisting of an alkali metal sulfate, alkali earth metal sulfate, transition metal sulfate and concentrated sulfuric acid, determining the spectrophotometric absorption of the reaction mixture formed, and determining the amount of the cholesterol lipoprotein subfraction present in the test sample based on the spectrophotometric absorption of the reaction mixture formed;
(c) reaction at least a portion of said clinical test sample with a Chugaev reagent and with an additive selected from the group consisting of dextran sulfate and an alkali metal perchlorate, and determining the spectrophotometric absorption of the reaction mixture formed, and determining the amount of the cholesterol lipoprotein subfraction present in the test sample based on the spectrophotometric absorption of the reaction mixture formed.

32. The clinical detection method of claim 31, wherein the Chugaev reagent is formed by adding sequentially to the test sample:
(1) acetyl chloride, and then
(2) zinc chloride, glacial acetic acid.

33. The clinical detection method as recited in claim 31, wherein steps (a), (b) and (c) are each performed.

34. A detection method as recited in claim 31, wherein:
said alkali metal sulfate is selected from the group consisting of lithium sulfate, sodium sulfate and potassium sulfate,
said transition metal sulfate is selected from the group consisting of scandium sulfate, titanium sulfate, chromium sulfate, manganese sulfate, nickel sulfate, zinc sulfate, copper sulfate and calcium sulfate, and
said alkali metal perchlorate is selected from the group consisting of lithium perchlorate, sodium perchlorate and potassium perchlorate.

35. A clinical detection method as recited in claim 32, wherein the acetyl chloride is added to a test sample before an alkali metal sulfate, alkali earth metal sulfate, transition metal sulfate, concentrated sulfuric acid, dextran sulfate or alkali metal perchlorate is added to the test sample.

36. A clinical detection method for determining the amount of cholesterol in a clinical test sample, the method comprising:

(a) forming an optically active colored Chugaev reaction product with cholesterol in the test sample;
(b) determining an amount of HDL cholesterol present in the test sample by CD absorption at a first wavelength, or alternatively, at a first and a second wavelength;
(c) determining an amount of LDL+VLDL cholesterol present in said sample by CD absorption at a third wavelength; and
(d) determining an amount of total cholesterol present in the test sample.

37. A clinical detection method for determining the amount of cholesterol present in a clinical test sample, the method comprising:
(a) forming an optically active colored Chugaev reaction product with cholesterol in the test sample;
(b) determining an amount of total cholesterol present in the test sample by spectrophotometric absorption at a certain wavelength;
(c) determining an amount of VLDL+LDL cholesterol present in the test sample by CD absorption at the same wavelength of step (b); and
(d) determining an amount of HDL cholesterol which is present in the test sample.

38. A clinical detection method for determining the amount of cholesterol in a test sample, the method comprising:
(a) forming an optically active Chugaev reaction product with cholesterol in the test sample;
(b) determining an amount of HDL-cholesterol in the test sample by CD absorption at a first wavelength, or alternatively, at a first and second wavelength;
(c) simultaneously determining an amount of LDL+VLDL cholesterol present in the test sample by CD absorption at a third wavelength; and
(d) determining an amount of total cholesterol which is present in the test sample by spectrophotometric absorption at the third wavelength.

* * * * *